US008431755B2

(12) United States Patent
Vauk

(10) Patent No.: US 8,431,755 B2
(45) Date of Patent: Apr. 30, 2013

(54) COMBINED FIRST AND SECOND GENERATION BIOFUELS PROCESS

(75) Inventor: Dennis A. Vauk, Houston, TX (US)

(73) Assignee: Air Liquide Large Industries U.S. LP, Houston, TX (US)

( * ) Notice: Subject to any disclaimer, the term of this patent is extended or adjusted under 35 U.S.C. 154(b) by 199 days.

(21) Appl. No.: 12/840,699

(22) Filed: Jul. 21, 2010

(65) Prior Publication Data

US 2012/0022299 A1    Jan. 26, 2012

(51) Int. Cl.
*C07C 1/00* (2006.01)
*C07C 7/00* (2006.01)

(52) U.S. Cl.
USPC ........... 585/240; 585/242; 585/733; 585/800; 44/605

(58) Field of Classification Search ................ 585/240, 585/242, 733, 800; 44/605; 48/127.7, 127.1
See application file for complete search history.

(56) References Cited

U.S. PATENT DOCUMENTS

| | | | | |
|---|---|---|---|---|
| 8,053,615 | B2* | 11/2011 | Cortright et al. | 585/240 |
| 8,101,383 | B2* | 1/2012 | Henriksen et al. | 435/72 |
| 8,133,393 | B2* | 3/2012 | Stuart | 210/606 |
| 8,148,579 | B2* | 4/2012 | Bradin | 568/387 |
| 8,158,833 | B2* | 4/2012 | Dumenil et al. | 568/840 |
| 8,212,087 | B2* | 7/2012 | Medoff | 568/878 |
| 8,216,430 | B2* | 7/2012 | Cheiky | 202/216 |
| 2008/0057555 | A1 | 3/2008 | Nguyen | |

OTHER PUBLICATIONS

PCT/US2011/044480, International Search Report and Written Opinion, Apr. 5, 2012.

P. Alvira, E. Tomas-Pejo, M. Ballesteros, M.J. Negro, "Pretreatment technologies for an efficient bioethanol production process based on enzymatic hydrolysis: A review," Bioresource Technology, Elsevier BV, GB, vol. 101, No. 13, Jul. 1, 2010, pp. 4851-4861.

Mustafa Balat, Mehmet Balat, Elif Kirtay, Hawa Balat, "Main routes for the thermo-conversion of biomass into fuels and chemicals. Part 1: Pyrolysis systems," Energy Conversion Management, Elsevier Science Publishers, Oxford, GB, vol. 50, No. 12, Dec. 1, 2009, pp. 3147-3157.

Ayhan Demirbas, "Biorefineries: Current activities and future developments," Energy Conversion and Management, Elsevier Science Publishers, Oxford, GB, vol. 50, No. 11, Nov. 1, 2009, pp. 2782-2801.

George W. Huber, Sara Iborra and Avelino Corma, "Synthesis of Transportation Fuels from Biomass: Chemistry, Catalysts, and Engineering," Chemical Reviews, American Chemical Society, US, vol. 106, No. 9, Sep. 1, 2006, pp. 4044-4098.

* cited by examiner

*Primary Examiner* — Nina Bhat
(74) *Attorney, Agent, or Firm* — Elwood L. Haynes

(57) ABSTRACT

A process to integrate a first biofuels process and a second generation cellulosic biofuels process is provided. The pyrolysis means which produces the char stream and a bioliquid stream. The low pressure hydrotreating component, a high pressure hydrotreating component, the low pressure hydrotreating component which produces the hydrocarbon stream, the high pressure hydrotreating component which produces the steam stream and bioliquid stream. A distillation means, which produces a green gasoline stream and a green diesel stream from the bioliquid stream. The second biofuels process may be a first generation bio-ethanol process, which produces a bio-ethanol stream. The hydrogen production unit, which produces the hydrogen stream and the steam stream. The hydrogen production unit may be a steam reformer or partial oxidation unit.

22 Claims, 6 Drawing Sheets

COMBINED FIRST AND SECOND GENERATION BIOFUELS PROCESS

BACKGROUND

Biofuels are a wide range of fuels which are in some way derived from biomass. The term covers solid biomass, liquid fuels and various biogases. Biofuels are gaining increased public and scientific attention, driven by factors such as oil price spikes, the need for increased energy security, and concern over greenhouse gas emissions from fossil fuels.

Bioethanol is an alcohol made by fermenting the sugar components of plant materials and it is made mostly from sugar and starch crops. With advanced technology being developed, cellulosic biomass, such as trees and grasses, are also used as feedstocks for ethanol production. Ethanol can be used as a fuel for vehicles in its pure form, but it is usually used as a gasoline additive to increase octane and improve vehicle emissions. Bioethanol is widely used in the USA and in Brazil.

Biodiesel is made from vegetable oils, animal fats or recycled greases. Biodiesel can be used as a fuel for vehicles in its pure form, but it is usually used as a diesel additive to reduce levels of particulates, carbon monoxide, and hydrocarbons from diesel-powered vehicles. Biodiesel is produced from oils or fats using transesterification and is the most common biofuel in Europe.

'First-generation biofuels' are biofuels made from sugar, starch, vegetable oil, or animal fats using conventional technology. Often, first-generation biofuels are produced by fermenting plant-derived sugars to ethanol, using a similar process to that used in beer and wine-making. The basic feedstocks for the production of first generation biofuels are often seeds or grains such as sunflower seeds, which are pressed to yield vegetable oil that can be used in biodiesel, or wheat, which yields starch that is fermented into bioethanol. These feedstocks could instead enter the animal or human food chain, and as the global population has risen their use in producing biofuels has been criticised for diverting food away from the human food chain, leading to food shortages and price rises.

This typically requires the use of 'food' crops such as sugar cane, corn, wheat, and sugar beet. These crops are required for food, so if too much biofuel is made from them, food prices could rise and shortages might be experienced in some countries. Corn, wheat and sugar beet also require high agricultural inputs in the form of fertilizers, which limit the greenhouse gas reductions that can be achieved.

Second generation biofuel technologies have been developed because first generation biofuels manufacture has important limitations. First generation biofuel processes are useful, but limited in most cases: there is a threshold above which they cannot produce enough biofuel without threatening food supplies and biodiversity. Many first generation biofuels are dependent of subsidies and are not cost competitive with existing fossil fuels such as oil, and some of them produce only limited greenhouse gas emissions savings. When taking emissions from production and transport into account, life cycle assessment from first-generation biofuels frequently exceed those of traditional fossil fuels.

Second generation biofuels can help solve these problems and can supply a larger proportion of our fuel supply sustainably, affordably, and with greater environmental benefits.

The goal of second generation biofuel processes is to extend the amount of biofuel that can be produced sustainably by using biomass consisting of the residual non-food parts of current crops, such as stems, leaves and husks that are left behind once the food crop has been extracted, as well as other crops that are not used for food purposes (non food crops), such as switch grass, jatropha and cereals that bear little grain, and also industry waste such as woodchips, skins and pulp from fruit pressing, etc.

The problem that second generation biofuel processes are addressing is to extract useful feedstocks from this woody or fibrous biomass, where the useful sugars are locked in by lignin and cellulose. All plants contain cellulose and lignin. These are complex carbohydrates (molecules based on sugar). Lignocellulosic ethanol is made by freeing the sugar molecules from cellulose using enzymes, steam heating, or other pre-treatments. These sugars can then be fermented to produce ethanol in the same way as first generation bioethanol production. The by-product of this process is lignin. Lignin can be burned as a carbon neutral fuel to produce heat and power for the processing plant and possibly for surrounding homes and businesses.

SUMMARY

In another embodiment, the first biofuels process is a second generation cellulosic biofuels process, which includes, but is not limited to the following. The pyrolysis means which produces the char stream and a bioliquid stream. The low pressure hydrotreating component, a high pressure hydrotreating component, the low pressure hydrotreating component which produces the stabilized hydrocarbon stream, the high pressure hydrotreating component which produces the steam stream and a bioliquid stream. A distillation means, which produces a green gasoline stream and a green diesel stream from the bioliquid stream. The second biofuels process may be a first generation bio-ethanol process, which produces a bio-ethanol stream. The hydrogen production unit, which produces the hydrogen stream and the steam stream. The hydrogen production unit may be a steam reformer or partial oxidation unit.

DESCRIPTION OF PREFERRED EMBODIMENTS

Figure 1:
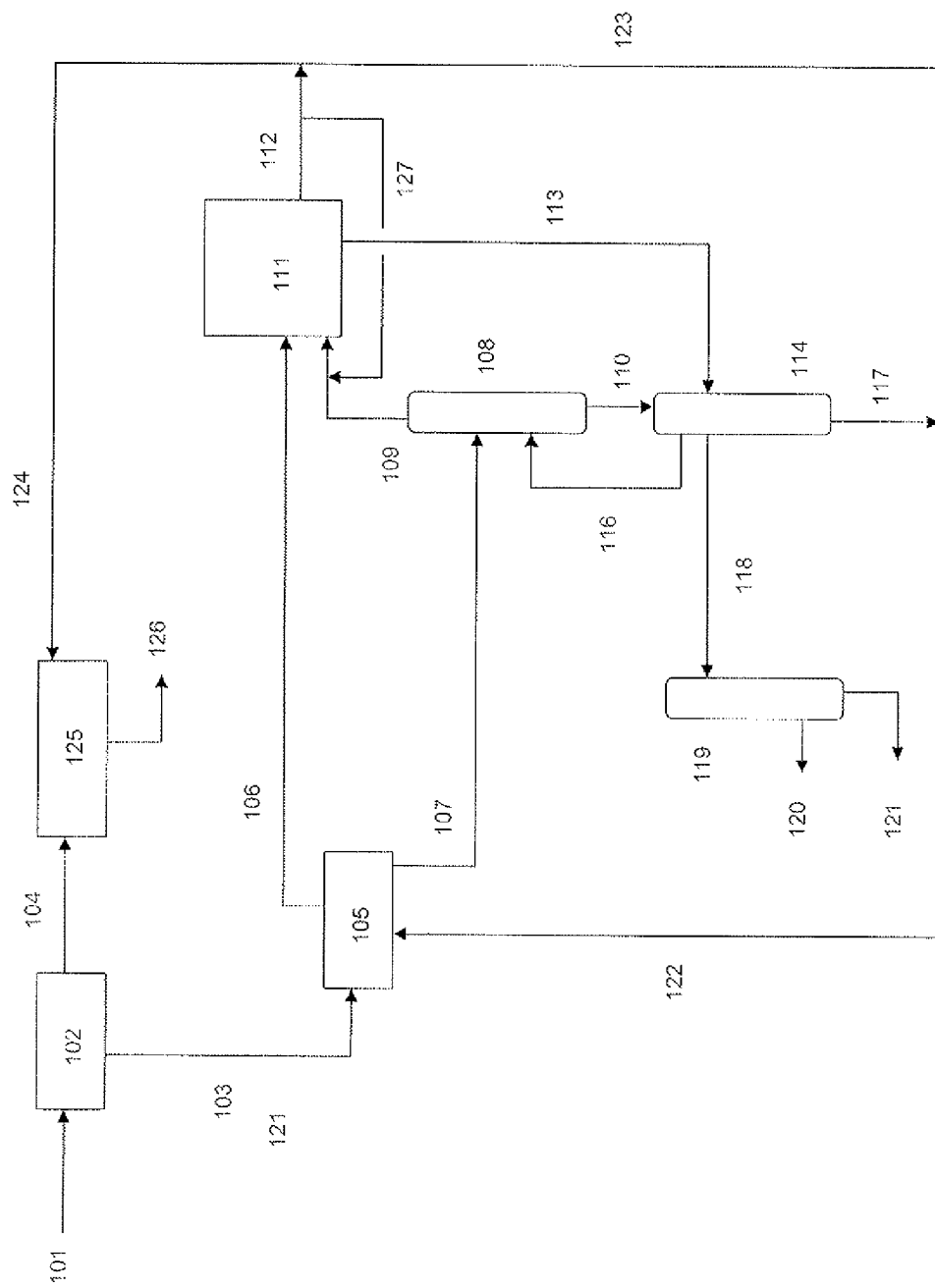
FIG. 1 illustrates one embodiment of the present invention.

Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning now to FIG. 1, the invention is a hybrid process for combining first generation biofuels technology with second generation biofuels technology. In particular, this is an integrated process for producing biofuels from a biofuel feedstock from a cellulosic component and a starch component. The cellulosic component 103 and a hydrogen stream 113 generated by a hydrogen production unit 111 are introduced into a first biofuels process. The starch component 104 and a steam stream 124 are introduced into a second biofuels process 125. A char stream 106 generated by a pyrolysis process 105 of the first biofuels process; and a hydrocarbon stream 109 generated by a low pressure hydrotreating component 108 are introduced into the hydrogen production unit 111.

In one embodiment, the steam stream 117, 112, 124 is generated by a high pressure hydrotreating component 114 of the first biofuels process and/or the hydrogen production unit 111. In another embodiment, the first biofuels process is a second generation cellulosic biofuels process. The second biofuels process may be a first generation bio-ethanol process.

Figure 2:
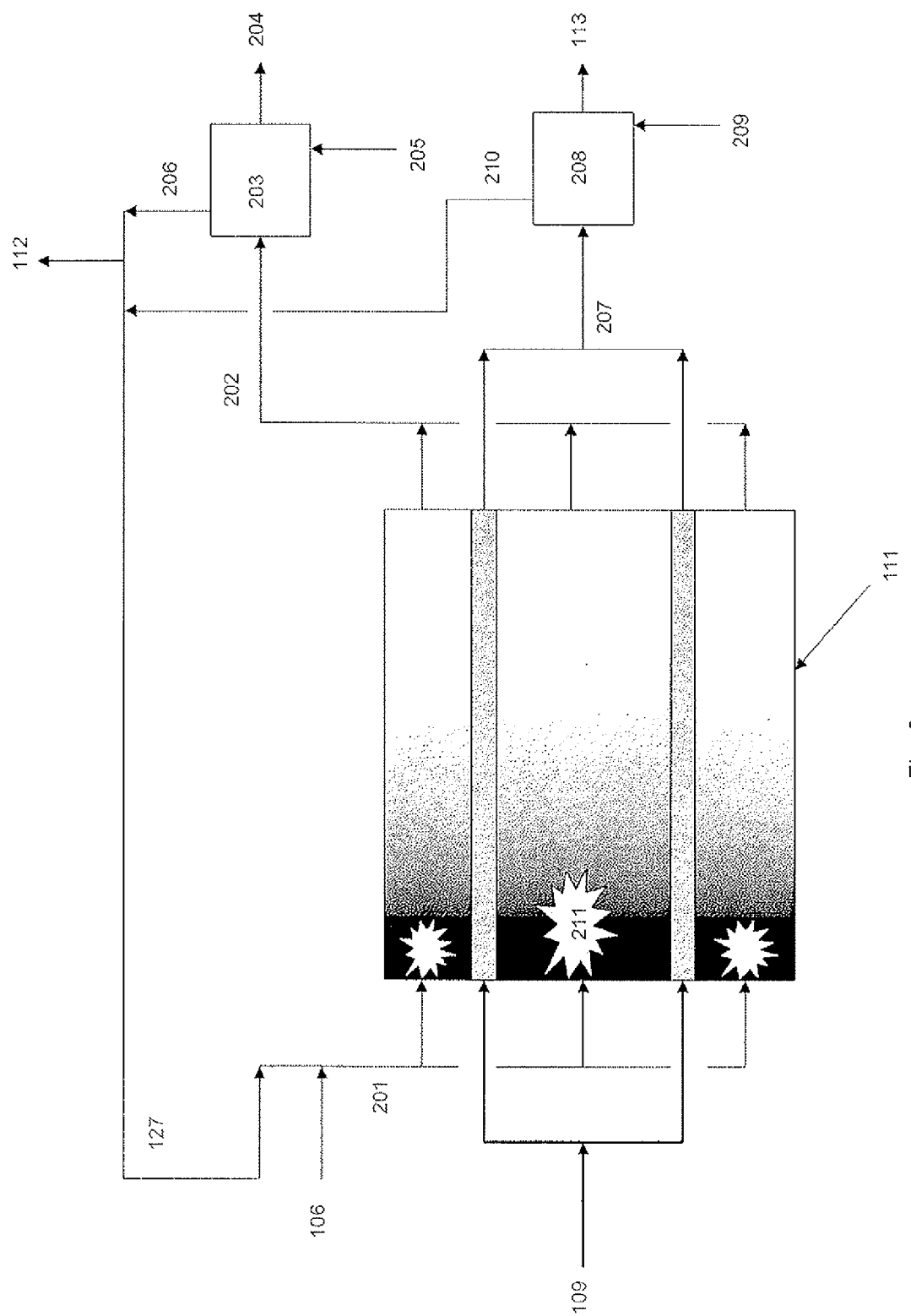
FIG. 2 illustrates details of one embodiment of the hydrogen production unit and the associated waste heat boilers.

In another embodiment, the first biofuels process is a second generation cellulosic biofuels process, which includes, but is not limited to the following. The pyrolysis means 105 which produces the char stream 106 and a bioliquid stream 107. The low pressure hydrotreating component 108, a high pressure hydrotreating component 114, the low pressure hydrotreating component which produces the hydrocarbon stream 109, the high pressure hydrotreating component 114 which produces the steam stream 117. A distillation means 119, which produces a green gasoline stream 120 and a green diesel stream 121 from the bioliquid stream 107. The second biofuels process may be a first generation bio-ethanol process, which produces a bio-ethanol stream 126. The hydrogen production unit 111, which produces the hydrogen stream 112 and the steam stream 112. The hydrogen production unit 111 may be a steam reformer Turning now to FIG. 2, the hydrogen production unit has a furnace 211, a process effluent stream 207, a flue gas stream 202, a feed stream and a fuel stream 201. The feed stream is the hydrocarbon stream 109, the fuel stream 201 is the char stream 106, and the feed is combined with the steam stream 127, which is produced from the hydrogen production unit 111, and fed to the furnace 211. In another embodiment, the process effluent stream 207 indirectly exchanges heat with a first feed water stream 209 in a first waste heat boiler 208 and the flue gas stream 202 indirectly exchanges heat with a second feedwater stream 205 in a second waste heat boiler 203 to produce the steam stream 112.

In another embodiment, the process effluent 207 is contacted with a catalyst 302 in a water gas shift reactor 301 to convert carbon monoxide to hydrogen and carbon dioxide, thereby producing a shift effluent 303. The shift effluent 303 and a first feed water stream 209 may be in indirect heat exchange in a first waste heat boiler 208 to produce the steam stream 112, thereby producing a cooled shift effluent 304. The cooled shift effluent 304 may be fed into a pressure swing adsorption (PSA) unit 305 to separate hydrogen from carbon monoxide, un-reacted hydrocarbons and carbon dioxide, thereby producing the hydrogen stream 113 and a PSA tail gas stream 306. The hydrogen stream 113 may be sent to the high pressure hydrotreating component 114, The PSA tail gas 306 may be sent to the furnace 211 wherein it is used as fuel for the furnace in combination with the char stream 106. The high pressure hydrotreating component 114 may be a bioliquid hydrotreater.

In one embodiment, at least a portion of the steam stream 112 is fed to the furnace 211 and at least a portion of the steams stream 112 produced is exported to the second biofuels process 125. In another embodiment the hydrogen production unit 111 may be a partial oxidation unit.

Figure 3:
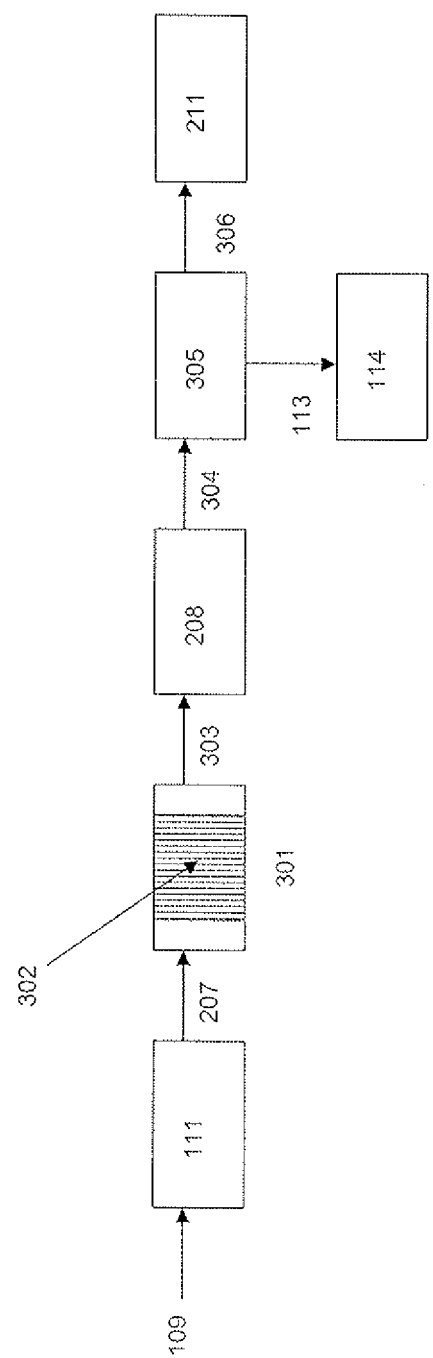
FIG. 3 illustrates one embodiment of water gas shift section of the present invention.

Turning now to FIG. 3, the PSA tail gas 306 may comprise carbon monoxide, un-reacted hydrocarbons and carbon dioxide and some portion of hydrogen.

Figure 4:
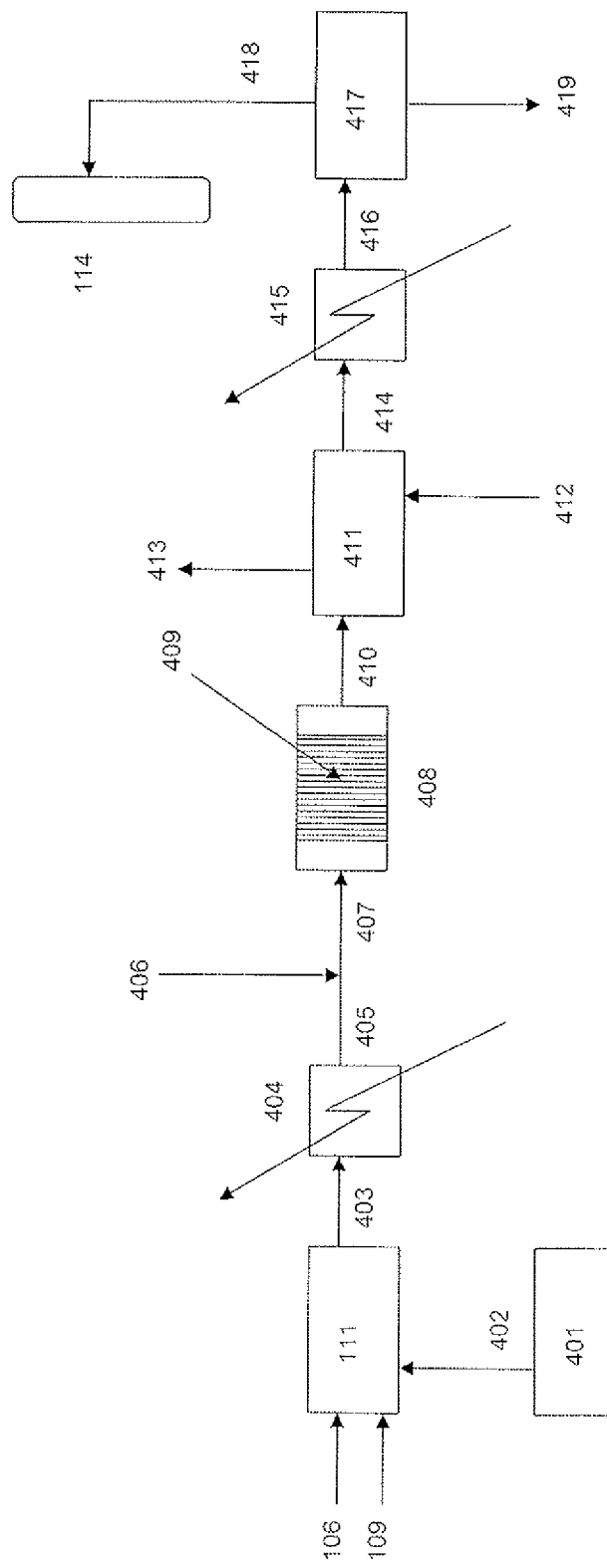
FIG. 4 illustrates another embodiment of the water gas shift section of the present invention.

Turning now to FIG. 4, the char stream 106 and the hydrocarbon stream 109 are introduced as feed. An oxygen stream 402, generated by air separation in a cryogenic process 401, is introduced into the partial oxidation unit 111. The oxygen stream 402, the char stream 106, and the hydrocarbon stream 109 are combined in the partial oxidation unit 111 thereby producing a syngas stream 403. The syngas stream 403 is cooled in a first heat exchanger 404 thereby creating a cooled syngas stream 405. The cooled syngas stream 405 is combined with a water stream or a steam stream 406, thereby producing a wet syngas stream 407. The wet syngas stream 407 is introduced into a water gas shift reactor 408 wherein a water gas shift reaction is promoted by contact with a catalyst 409, thereby producing a shifted syngas stream 410. The shifted gas stream 410 and a feed water stream 412 exchange heat in an indirect contact waste heat boiler 411 to produce a steam stream 413, thereby producing a cooled shifted syngas stream 414. The cooled shifted syngas stream 414 is further cooled in an air cooler 415, thereby producing a further cooled shifted syngas stream 416. The further cooled shifted syngas stream 416 is introduced into a first absorbtion unit 417 where a hydrogen stream 418 is separated from a first off-gas stream 419.

In another embodiment, the syngas stream 403 comprises hydrogen, carbon monoxide and carbon dioxide. In another embodiment, the catalyst 409 promotes the conversion of carbon monoxide to hydrogen to produce a shifted syngas 410 with at least 90% of the carbon monoxide converted to hydrogen. The first adsorption unit 417 may be of a pressure swing adsorption (PSA) unit producing hydrogen with a purity of greater than 99.5%. The hydrogen stream 418 may be sent to the bioliquid hydrotreater.

Figure 5:
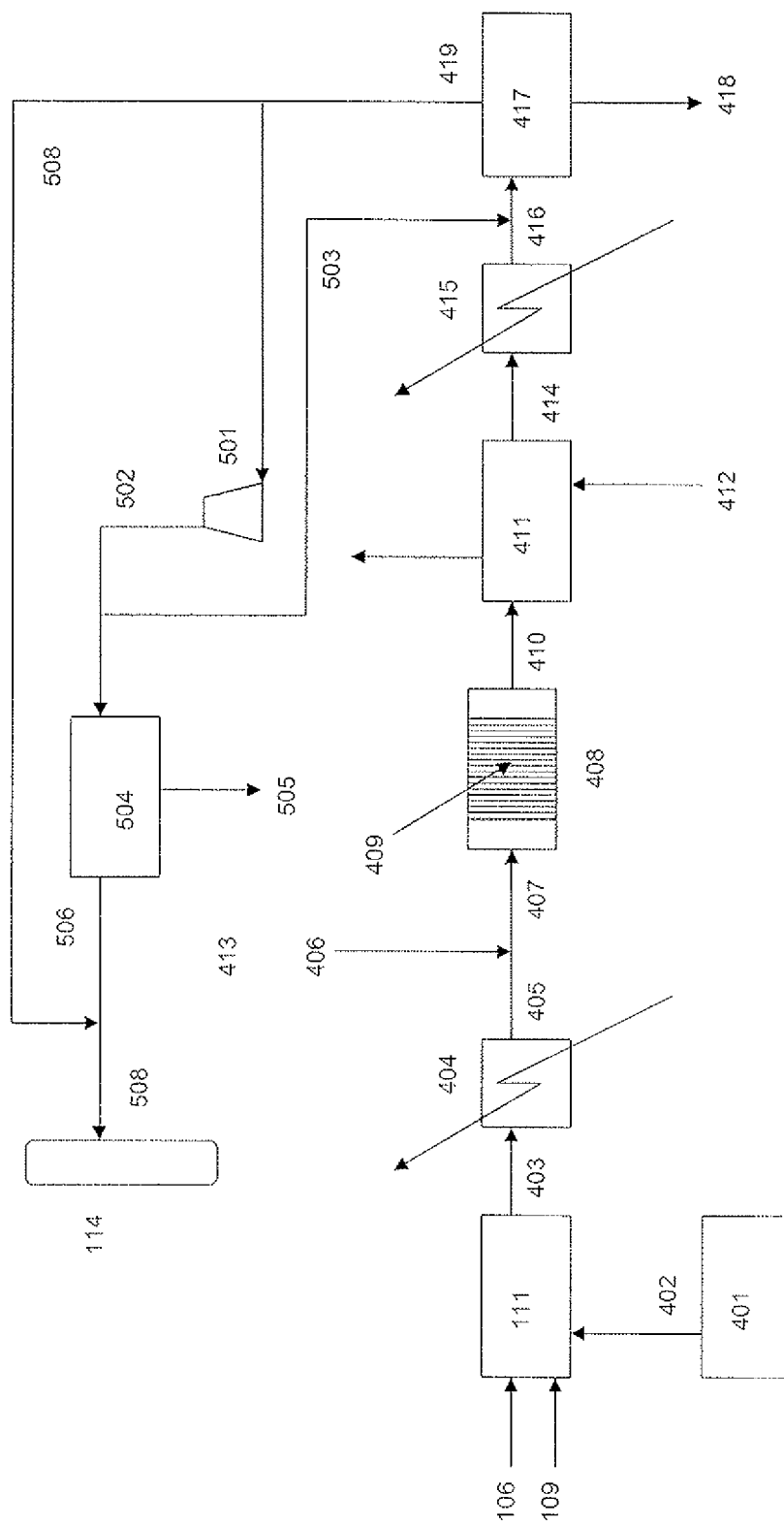
FIG. 5 illustrates another embodiment of the water gas shift section of the present invention.

Turning now to FIG. 5, the first off-gas stream 418, comprises a PSA tail gas consisting of carbon monoxide, carbon dioxide, unreacted hydrocarbon, nitrogen and argon impurities of the oxygen stream. At least part of the first off-gas stream 419 is compressed in a compressor 501 thereby producing a compressed off-gas stream 502, and a remainder stream 508. The compressed off-gas stream 502 is recycled to the first adsorption unit 417 for further recovery of hydrogen or sent to a second adsorption unit 504 for further recovery of hydrogen, and thereby producing a second off-gas stream 506, and a second hydrogen stream 505. The remainder stream 508 and the second off-gas stream 506 are combined to form a combined off-gas stream 506. The combined off-gas stream 506 is sent to the bioliquid hydrotreater 114 to be used as fuel in furnaces within the bioliquid hydrotreater and/or the fractionation section. The second adsorption unit 504 may be a PSA.

Figure 6:
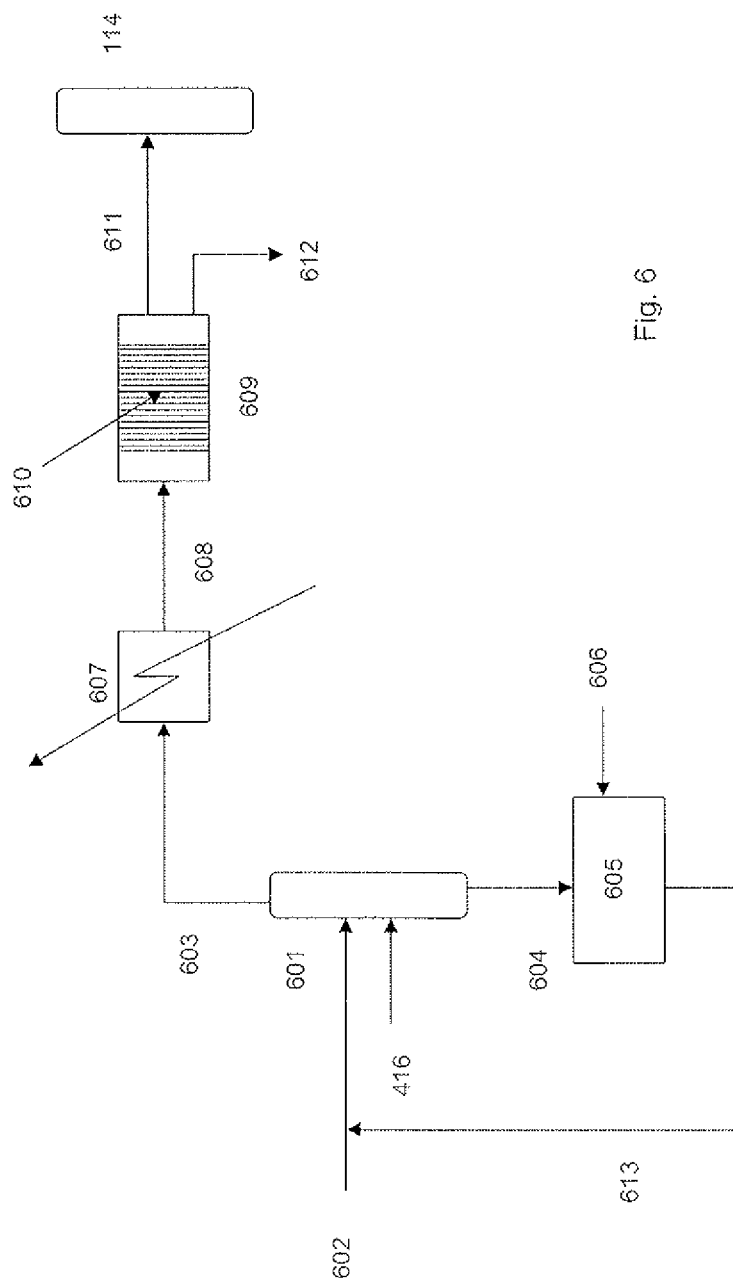
FIG. 6 illustrates another embodiment of the water gas shift section of the present invention.

Turning now to FIG. 6, the first adsorption unit 417 comprises an absorber 601 for the removal of carbon dioxide and further purification of hydrogen. The carbon dioxide is removed in the absorber 601, by contacting the cooled shifted syngas stream 416 with an activated MDEA stream 602, or similar solvent stream, thereby producing a purified hydrogen stream 603 from the overhead of the absorber 601 and a rich solvent stream 604 from the bottom of the absorber 601. The rich solvent stream 604 is sent to a regenerator 605 where a steam stream 606 is used to regenerate the solvent stream 604 thereby producing a regenerated solvent stream 613 which is returned to the absorber 601. The purified hydrogen stream 603 is heated in a heat exchanger 607, thereby producing a heated purified hydrogen stream 608, which is sent to a methanation reactor 609 where it is contacted with a catalyst 610 to promote the reaction of remaining carbon monoxide and carbon dioxide to produce a methane stream 612 and a further purified hydrogen stream 611. The further purified hydrogen stream 611 has a purity of greater than 97%, and the further purified hydrogen stream 611 is sent to the high pressure hydrotreating component 114.

The biofuels production process 100, includes providing a biofuel feedstock 101, comprising a cellulosic component 103 and a starch component 104, separating the cellulosic component 103 from the starch component 104, introducing the cellulosic component 103 to a pyrolysis process 105, thereby producing at least a char stream 106 and a bio-oil stream 107, introducing the bio-oil stream 107 and a purge hydrogen stream 116 into a low pressure hydrotreating process 108, thereby producing a first intermediate liquid stream 110, and a hydrocarbon stream 109, introducing the first intermediate liquid stream 110 and a hydrogen stream 113 into a high pressure hydrotreating process 114, thereby producing a second intermediate liquid stream 118, the purge hydrogen stream 116, and the steam stream 117, introducing the second intermediate liquid stream 118 to a distillation column 119, thereby producing a product green gasoline stream 120 and a product green diesel stream 121, introducing the char stream 106, the hydrocarbon stream 109, into a hydrogen production unit 111, thereby producing the hydrogen stream 113, and a second steam stream 112, combining the steam stream 117 and the second steam stream to form combined steam stream 124, introducing the starch component 104, and the combined steam stream 124 into an ethanol plant 125, thereby producing a bio-ethanol stream 126.

The system for producing biofuels, includes a feedstock separation means 102, a pyrolysis means 105, a low pressure hydrotreating means 108, a high pressure hydrotreating means 114, a distillation column 119, a hydrogen production means 111, an ethanol plant 125; a means for providing a biofuel feedstock 101, comprising a cellulosic component 103 and a starch component 104, a means for introducing the cellulosic component 103 to the pyrolysis means 105, thereby producing at least a char stream 106 and a bio-oil stream 107, a means for introducing the bio-oil stream 107 and a means for providing a purge hydrogen stream 116 into the low pressure hydrotreating means 108, thereby producing a first intermediate liquid stream 110, and a hydrocarbon-containing stream 109, a means for introducing the first intermediate liquid stream 110 and a means for introducing a hydrogen stream 113 into the high pressure hydrotreating process 114, thereby producing a second intermediate liquid stream 118, the purge hydrogen stream 116, and the steam stream 117, a means for introducing the second intermediate liquid stream 118 to the distillation column 119, thereby producing a product green gasoline stream 120 and a product green diesel stream 121, a means for introducing the char stream 106, a means for introducing the hydrocarbon-containing stream 109, into the hydrogen production means 111, thereby producing the hydrogen stream 113 and a second steam stream 112, a means for combining the steam stream 117 and the second steam stream 112, and a means for introducing the starch component 104, and a means for introducing a combined steam stream 124 into the ethanol plant.

What is claimed is:

1. An integrated process for producing biofuels from a biofuel feedstock, comprising a cellulosic component and a starch component, the process comprising:
   introducing the cellulosic component and a hydrogen stream generated by a hydrogen production unit, into a first biofuels process,
   introducing the starch component and a steam stream into a second biofuels process,
   introducing a char stream generated by a pyrolysis of the first biofuels process; and a hydrocarbon stream generated by a low pressure hydrotreating component into the hydrogen production unit.

2. The process of claim 1, wherein said steam stream is generated by a high pressure hydrotreating component of the first biofuels process and/or the hydrogen production unit.

3. The process of claim 1, wherein the first biofuels process is a second generation cellulosic biofuels process.

4. The process of claim 1, wherein the second biofuels process is a first generation bio-ethanol process.

5. The process of claim 1, wherein:
   the first biofuels process is a second generation cellulosic biofuels process comprising:
      the pyrolysis means, the pyrolysis means producing the char stream and a bioliquid stream,
      the low pressure hydrotreating component, a high pressure hydrotreating component, the low pressure hydrotreating component producing the hydrocarbon stream, the high pressure hydrotreating component producing the steam stream, and
      a distillation means, producing a green gasoline stream and a green diesel stream from the bioliquid stream,
   the second biofuels process is a first generation bio-ethanol process, producing a bio-ethanol stream, and
   the hydrogen production unit, produces the hydrogen stream and the steam stream.

6. The process of claim 1, where the hydrogen production unit is a steam reformer.

7. The process of claim 5 wherein the hydrogen production unit has a furnace, a process effluent stream, a flue gas stream, a feed stream and a fuel stream, wherein the feed stream is the hydrocarbon stream, the fuel stream is the char stream, and the feed is combined with the steam stream, produced from the hydrogen production unit, and fed to the furnace.

8. The process of claim 7 where the process effluent stream indirectly exchanges heat with a first feed water stream in a first waste heat boiler and the flue gas stream indirectly exchanges heat with a second feedwater stream in a second waste heat boiler to produce the steam stream.

9. The process of claim 7 further comprising:
   contacting the process effluent with a catalyst in a water gas shift reactor to convert carbon monoxide to hydrogen and carbon dioxide, thereby producing a shift effluent,
   indirectly exchanging heat between the shift effluent and a first feed water stream in a first waste heat boiler to produce the steam stream, thereby producing a cooled shift effluent,
   feeding the cooled shift effluent into a pressure swing adsorption (PSA) unit to separate hydrogen from carbon monoxide, un-reacted hydrocarbons and carbon dioxide, thereby producing the hydrogen stream and a PSA tail gas stream,
   sending the hydrogen stream to the high pressure hydrotreating component, and sending the PSA tail gas to the furnace wherein it is used as fuel for the furnace in combination with the char stream.

10. The process of claim 9, wherein the high pressure hydrotreating component is a bioliquid hydrotreater.

11. The process of claim 9, wherein the PSA tail gas comprises carbon monoxide, un-reacted hydrocarbons and carbon dioxide and some portion of hydrogen.

12. the process of claim 9 where at least a portion of the steam stream is fed to the furnace and at least a portion of the steams stream produced is exported to the second biofuels process.

13. The process of claim 5 where the hydrogen production unit consists of a partial oxidation unit.

14. The process of claim 13 wherein the partial oxidation unit further comprises:
introducing the char stream and the hydrocarbon stream as feed,
generating an oxygen stream by air separation in a cryogenic process and introducing the oxygen stream into the partial oxidation unit,
combining the oxygen stream, the char stream, and the hydrocarbon stream in the partial oxidation unit thereby producing a syngas stream,
cooling the syngas stream in a first heat exchanger thereby creating a cooled syngas stream,
combining the cooled syngas stream with a water stream or a steam stream, thereby producing a wet syngas stream,
introducing the wet syngas stream into a water gas shift reactor wherein a water gas shift reaction is promoted by contact with a catalyst, thereby producing a shifted syngas stream,
indirectly exchanging heat between the shifted gas stream and a feed water stream in a waste heat boiler to produce a steam stream, thereby producing a cooled shifted syngas stream,
further cooling the cooled shifted syngas stream in an air cooler, thereby producing a further cooled shifted syngas stream, and
sending said further cooled shifted syngas stream to a first absorbtion unit where a hydrogen stream is separated from a first off-gas stream.

15. The process of claim 14, wherein the syngas stream comprises hydrogen, carbon monoxide and carbon dioxide.

16. The process of claim 14, wherein the catalyst promotes the conversion of carbon monoxide to hydrogen to produce a shifted syngas with at least 90% of the carbon monoxide converted to hydrogen.

17. The process of claim 14 where the first adsorption unit consists of a pressure swing adsorption (PSA) unit producing hydrogen with a purity of greater than 99.5%.

18. The process of claim 14, wherein the hydrogen stream is sent to the bioliquid hydrotreater.

19. The process of claim 14, wherein the first off-gas stream, comprising a PSA tail gas consisting of carbon monoxide, carbon dioxide, unreacted hydrocarbon, nitrogen and argon impurities of the oxygen stream, comprising:
compressing at least part of the first off-gas stream in a compressor thereby producing a compressed off-gas stream, and a remainder stream and
recycling the compressed off-gas stream to the first adsorption unit for further recovery of hydrogen or
sending the compressed off-gas stream to a second adsorption unit for further recovery of hydrogen, and thereby producing a second off-gas stream, and a second hydrogen stream,
combining the remainder stream and the second off-gas stream to form a combined off-gas stream, and
sending the combined off-gas stream to the bioliquid hydrotreater to be used as fuel in furnaces within the bioliquid hydrotreater and/or the fractionation section.

20. The process of claim 14 wherein the second adsorption unit is a PSA.

21. The process of claim 14 wherein the first adsorption unit comprises an absorber for the removal of carbon dioxide and further purification of hydrogen comprising:
removing carbon dioxide in the absorber, by contacting the cooled shifted syngas stream with an activated MDEA stream, or similar solvent stream, thereby producing a purified hydrogen stream from the overhead of the absorber and a rich solvent stream from the bottom of the absorber,
sending the rich solvent stream to a regenerator where a steam stream is used to regenerate the solvent stream thereby producing a regenerated solvent stream which is returned to the absorber,
heating the purified hydrogen stream in a heat exchanger, thereby producing a heated purified hydrogen stream, which is sent to a methanation reactor where it is contacted with a catalyst to promote the reaction of remaining carbon monoxide and carbon dioxide to produce a methane stream and a further purified hydrogen stream, wherein the further purified hydrogen stream has a purity of greater than 97%, and the further purified hydrogen stream is sent to the high pressure hydrotreating component.

22. A biofuels production process, comprising:
providing a biofuel feedstock, comprising a cellulosic component and a starch component,
separating the cellulosic component from the starch component,
introducing the cellulosic component to a pyrolysis process, thereby producing at least a char stream and a bio-oil stream,
introducing the bio-oil stream and a purge hydrogen stream into a low pressure hydrotreating process, thereby producing a first intermediate liquid stream, and a hydrocarbon stream,
introducing the first intermediate liquid stream and a hydrogen stream into a high pressure hydrotreating process, thereby producing a second intermediate liquid stream, the purge hydrogen stream, and the steam stream,
introducing the second intermediate liquid stream to a distillation column, thereby producing a product green gasoline stream and a product green diesel stream,
introducing the char stream, the hydrocarbon stream, into a hydrogen production unit, thereby producing the hydrogen stream, and a second steam stream,
combining the steam stream and the second steam stream to form combined steam stream,
introducing the starch component, and the combined steam stream into an ethanol plant, thereby producing a bio-ethanol stream.

* * * * *